United States Patent [19]

Allen

[11] Patent Number: 5,733,288
[45] Date of Patent: Mar. 31, 1998

[54] BONE BRUSH

[75] Inventor: Ronald C. Allen, Foster City, Calif.

[73] Assignee: Cohort Medical Products Group, Inc., Hayward, Calif.

[21] Appl. No.: 503,873

[22] Filed: Jul. 18, 1995

[51] Int. Cl.⁶ .................................................. A61B 17/56
[52] U.S. Cl. .................................................. 606/79; 606/53
[58] Field of Search .............................. 606/79, 85, 180; 15/28, 88, 104.05, 104.2, 179

[56] References Cited

U.S. PATENT DOCUMENTS

| | | | |
|---|---|---|---|
| 2,881,763 | 8/1959 | Robbins | 606/131 |
| 3,335,444 | 8/1967 | Weiler | 15/179 |
| 3,442,555 | 5/1969 | Cook | 300/21 |
| 3,874,017 | 4/1975 | Parker | 15/182 |
| 5,177,824 | 1/1993 | Vrignaud et al | 15/22.1 |
| 5,177,827 | 1/1993 | Ellison | 15/22.1 |
| 5,323,305 | 6/1994 | Montabaur et al. | 15/179 |
| 5,357,987 | 10/1994 | Schrepf | 132/218 |

Primary Examiner—Michael Buiz
Assistant Examiner—David O. Reip
Attorney, Agent, or Firm—James E. Eakin

[57] ABSTRACT

The present invention is a surgical bone brush which provides a means to remove soft tissue from harvested autogenous and allografts bone prior to implantation of the bone into the human body. The invention is a surgical instrument with multiple fibers of surgical grade stainless steel or implantable material, wherein the fibers are held in place around a retaining ring, by a cap assembly, and extend outward forming a brush. The bone brush head, provided in a plurality of sizes and shapes, is attached at one end of a shaft, of a length and diameter providing for the insertion of the shaft into surgical grade rotary hand pieces. The bone brush provides a means to remove soft tissue from bone, decorticate, and contour bone. This is achieved when the shaft of the bone brush is inserted into a surgical rotary hand piece and the hand piece is activated thereby causing the brush head to rotate. When the fibers of the bone brush are placed into contact with the soft tissue covering bone, the rotary action of the brush head removes the soft tissue from the bone. Decortication and bone contouring are achieved in the same manner.

4 Claims, 3 Drawing Sheets

BONE BRUSH

FIELD OF INVENTION

The invention relates to a method and instrument to denude, decorticate, and contour allograft and autograft bone for implantation into the human body.

BACKGROUND OF THE INVENTION

In the treatment of with conditions such as vertebral displacement, spondylosthesis, rotation of the vertebrae, segmental instability, disc degeneration, fractures, congenital defects, and tumors, it is common for the surgeon to denude, decorticate and shape the host bone to develop a base to apply graft bone. In order to achieve bone fusion or osteogenisis, there must be a bone to bone contact surface between the host bone and the bone graft. To achieve such a contact surface, soft tissue normally found on bone, such as periosteium, muscle, ligament and fibrous tissue must be removed from the contact point of both the host and graft bone. It has been well documented in the clinical literature that soft tissue retards, if not totally prevents the connection of bone cells, when obstructed by the presence of soft tissue. Such retardation or prevention of the passage of the bone cells may cause the fusion procedure to fail thereby resulting in a negative impact on the health of the patient.

Bone graft refers to the removal of bone from one location in a patient and subsequently placed in another location in the same patient. This type of bone graft is commonly called a autograft. Allograft bone is bone taken from one patient or a cadaver and implanted into another patient. This type of bone graft is commonly used to treat patients with insufficient bone or damaged bone.

In addition to meeting the requirements to remove soft tissue from bone, surgeons are often required to remove some of the cortical bone layer from the bone graft site and the bone graft. Decortication is being performed with instruments which do not provide a means to control the amount of cortical bone being removed. With little control of the bone removal process, surgeons can often take too much or too little cortical bone which leads to different surgical results.

When autografts are used, surgeons are often required to contour the autograft to meet the size requirements of the patient. Until the present invention, surgeons did not have an effective method or instrument to contour bone without the loss the of significant quantities of the needed bone or bone graft.

Surgeons continued to search for a means to effectively remove soft tissue from host bone without removing significant quantities of the bone stock itself as well as a means to decorticate and contour bone in an efficient manner.

DESCRIPTION OF PRIOR ART

Prior art devices for denuding, decorticating and shaping bone generally incorporated one of five basic design elements; fluted bone burrs, saw blades with various tooth configurations, bone cutting rongures, scalpels and cautery devices. While some such instruments have been used to remove soft tissue and shape bone, each is functionally limited in providing an effective means to remove soft tissue from bone.

As an example of prior art, bone burrs have been commonly used to decorticate autografts and allografts. However, to remove soft tissue from bone, bone burrs require significant force and high speed rotation of the burr. The force applied, as well as the high speed rotation of the burr, generates heat at the contact point where the burr is placed on the bone. Such heat increases the potential for the onset of thermal necrosis. Additionally, such prior art devices commonly require the application of water during its use to reduce the heat build-up. The use of water decreases the visibility within the operative area and thereby creates a potential surgical problem.

An earlier prior art device, the bone saw blade, was designed to cut bone in a straight line. Though the saw blade can effectively cut bone, it is ineffective and impractical to use a saw blade to remove layers of soft tissue from bone. Attempts at such removal generally result in loss of bone stock and very little removal of the soft tissue. Further, the use of saw blades do not provide a means to contour round bone or bone grafts.

An example of a prior art manual instrument device is represented by the bone cutting rongure. This instrument can be used to remove soft tissue from bone and has been used for this purpose. Such use however, requires that the jaws of the device bite into the bone itself and thereby remove bone material in the process of removing soft tissue. The use of such a device is both time consuming and ineffective when small autograft or allograft are being used. Additionally, when bone cutting rongures are used, the volume of bone loss is significantly higher than with the current invention.

Though not designed for use as a soft tissue removal device, the electro-cautery device effectively burns soft tissue away from bone. However, this device creates a significant amount of heat at the contact point of the cautery tip on the bone. Such large amounts of heat generation increase the potential of terminal necrosis at the bone contact point. Prior art devices used to remove soft tissue, decorticate and or shape bone, do not allow sufficient control of the amount of soft tissue removed as compared to the amount of bone removed or the device creates significant heat at the bone/device interface, thereby increasing the potential for a negative clinical result. All of these drawbacks are materially reduced by use of the invention. There has thus been a long felt need in the medical profession to provide a means to remove soft tissue from human bone that does not cause excessive heating of the bone, removal of significant amounts of the bone stock, and decreases the time required to contour bone.

SUMMARY OF THE INVENTION WITH OBJECTS

In view of the foregoing factors and consideration of the characteristics of the prior art, the primary objective of the present invention is to provide a fast, more efficient and effective instrument and method for removal of soft tissue from autograft and allograft bone, decortication, and contour of bone graft sites and bone grafts.

In the present invention, the bone brush is defined as having a solid shaft in a plurality of lengths and diameters with a brush head firmly attached at one end of the shaft. The solid shaft is provided as a means for inserting the bone brush instrument into a surgical rotary hand piece. A surgical hand piece can be pneumatic, battery or electrically powered and provides rotary action, at variable speeds, in compliance with the application method.

In one aspect of the invention the brush fibers are woven around a locking ring which is held in the brush cap assembly. The brush cap assembly can be of various diameters and shapes that provide for optional surgical uses. Both end caps, the solid shaft, locking ring, and brush fibers are manufactured from surgical grade stainless steel or other known materials acceptable for implantation in the human body. Individuals knowledgeable in the art are aware of a variety of materials such as composites, titanium, nitinol, and other alloys which can be used in the manufacture of the current invention.

Another object of the current invention is the means the upper and lower end cap are secured over the retaining ring containing the woven brush fibers and locked onto the proximal end of the bone brush shaft. Thereby creating a brush head assembly. The brush cap assembly, having been firmly attached to the shaft, will rotate at the same revolutions per minute as that of the shaft. When the invention is inserted into a surgical rotary hand piece and the revolutions per minute selected, the invention will rotate at the selected speed. The object of the current invention is that when the fibers are placed into contact with the soft tissue covering the bone, the fibers of the brush remove the soft tissue from the surface of the bone.

The described embodiment of this design ensures both the secure attachment of brush fibers to the instrument, as well as, inertial concentricity of fibers during rotary application.

In another object of the invention there is the method of denuding decorticating and or shaping bone with the instrument of the invention. The method according to the teachings of the present invention is to place the shaft of the current invention into a surgical rotary action hand piece and operate the hand piece at a speed sufficient to complete the removal of the soft tissue, from the graft site and graft bone. In the case of small bone grafts, the graft is held with a bone clamp or other similar instrument and the invention is applied to the graft as mentioned above.

In another object of the method, the invention is applied to the bone to provide a means to remove cortical bone from the external wall of host and graft bone. Following the removal of the soft tissue, the rotating fibers of the current invention is lightly applied to the bone at a higher rate of speed and worked in a longitudinal direction along the bone until the soft cancellous bone is visible. The brush fibers pick-up and retain the cortical bone until the bone fibers are full at which time the material is extracted from the fibers.

In another object of the method, the invention is applied to the bone to provide a means to contour bone on the external wall of the host and graft bone. The rotating fibers of the current invention is lightly applied to the bone at a higher rate of speed and worked in the desired direction along the bone until the desired shape has been achieved.

BRIEF DESCRIPTION OF THE DRAWINGS

The invention will be further disclosed with reference to the accompanying drawings, wherein.

DESCRIPTION OF PREFERRED EMBODIMENTS

Figure 1:
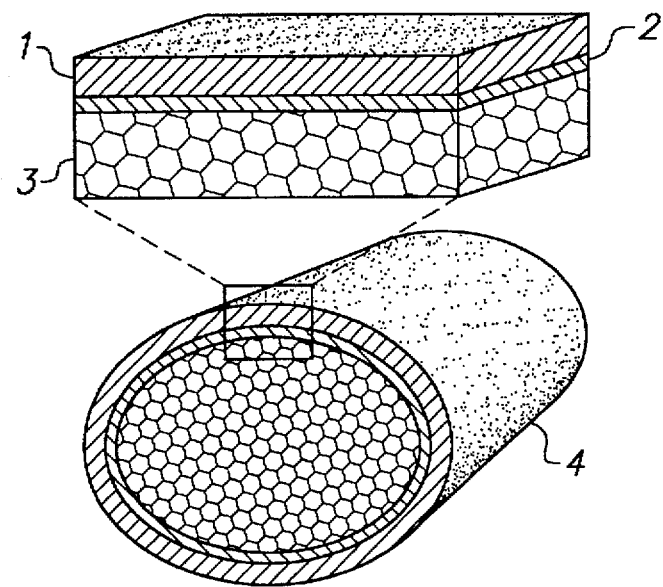
FIG. 1 is a cross section schematic representation of a round bone found in the human body(4) and the various layers presented in a further cross section of soft tissue layer(1), cortical bone layer(2) and cancellous bone(3).
Figure 2:
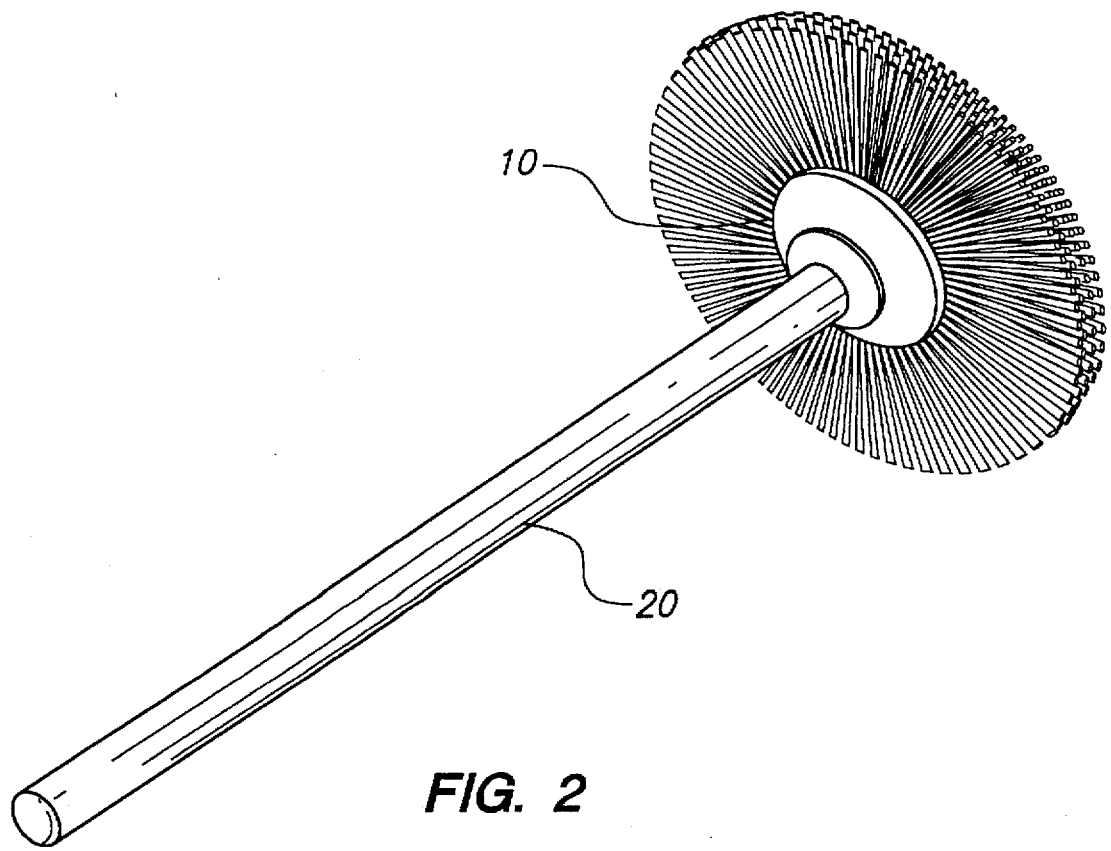
FIG. 2 is a side elevation of the bone brush according to the invention showing brush shaft(20), brush cap assembly (10). This figure presents the current invention in an assembled state.

Referring to the drawings, FIG. 1, a schematic view of human bone tissue which has been further presented in a cross section view wherein the soft tissue layer(1) covers the external wall of the cortical bone surface(2) which covers the cancellous bone(3). FIG. 2 is a side elevation of the current invention wherein the shaft of the bone brush(20) is attached to the brush cap assembly(10). Both the preferred brush shaft and the preferred brush cap assembly are manufactured from surgical stainless steel or other materials acceptable for implantation into the human body.

Figure 3:
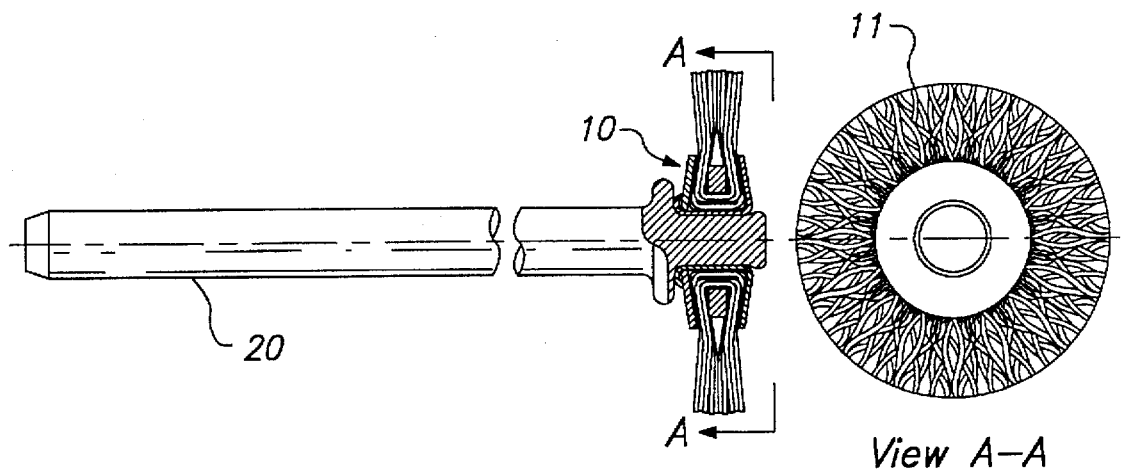
FIG. 3 is a side elevation view of the invention presented in cross section and in an axial view(AA). From the axial view, the round brush fiber head(11) is presented wherein the fibers extend outward from the brush cap assembly forming a circular shape. The brush cap assembly(10) is locked to the proximal end of the brush shaft(20).

Referring now to FIG. 3, the bone brush is presented in a side view where brush cap assembly (10) is positioned on to the brush shaft(20). Further, the preferred invention in the A—A view, presents the round brush fiber head(11) in the preferred form.

Figure 4:
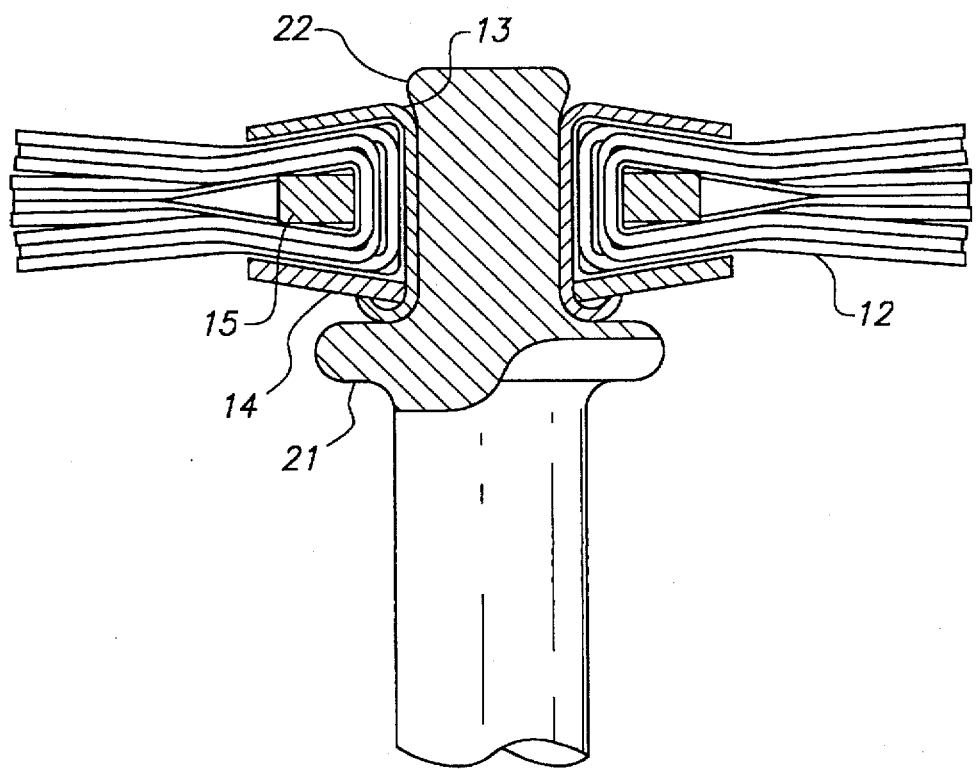
FIG. 4 is a cross section of the proximal end of the invention presenting the brush fiber locking ring(15), brush fibers(12) top(13) and bottom(14) locking caps presenting the captivity of the brush fibers.

Referring to FIG. 4, a cross sectional view of the preferred invention wherein brush cap assembly(10) is resting on assembly locking platform(21). The locking platform is larger in diameter than the brush shaft(20) thereby restricting the brush cap assembly from moving down the brush shaft. The proximal end of shaft head(22) is compressed with a rivet tool to spread the proximal portion of the brush shaft head, thereby locking the brush cap assembly onto the brush shaft. The brush cap assembly is comprised of brush fibers (12) which are woven over locking ring for brush fibers(15) forming the fiber brush. The brush fibers(12), after being woven over the locking ring(15) are prevented from migrating by the top locking cap(13) and the bottom locking cap(14). The bottom cap is applied to the underside of the fibers(12) and the top cap is applied over the lip of the bottom cap and bent to lock together the locking ring(15) brush fibers(12) which form the brush cap assembly(10).

Figure 5:
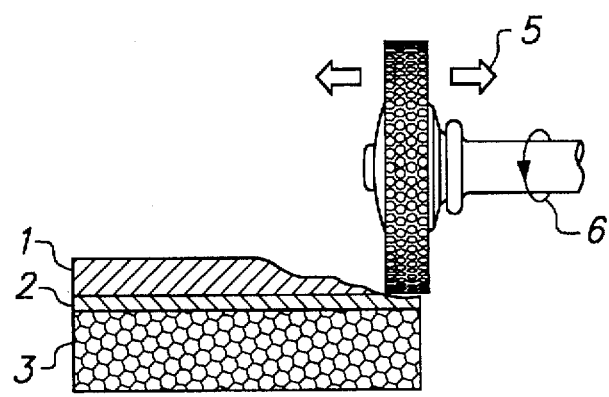
FIG. 5 is a schematic of application method of the invention to soft tissue. Further, the schematic presents the movement of the brush(5) and the active rotation of the invention(6).

Referring now to FIG. 5, a schematic view of the preferred method the current invention is applied to remove soft tissue(1) from bone(2) where the bone brush, after being attached to a surgical rotary hand piece, is rotated in a circular manner(6) and applied to the soft tissue covering of bone in a back and forth manner(5) thereby removing the soft tissue from the bone.

Figure 6:
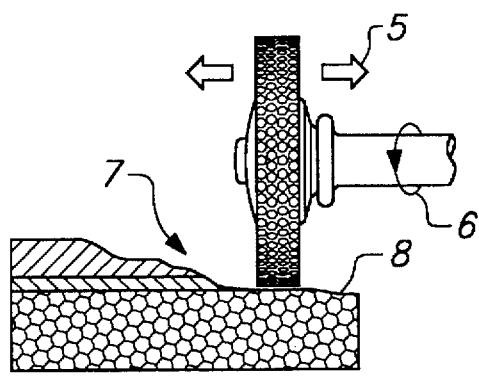
FIG. 6 is a schematic application method view of the invention further presenting the action of the invention in the removal of cortical bone layer(8) and soft tissue layer(7).

Referring now to FIG. 6, a schematic view of the preferred method the current invention is applied to remove both soft tissue(1) and cortical bone(2) from cancellous bone(3) where the bone brush, after being attached to a surgical rotary hand piece, is rotated in a circular manner(6) and applied to soft tissue covering of bone in a back and forth manner(5) thereby removing the soft tissue(1) and cortical bone(2) from cancellous bone(3).

Figure 7:
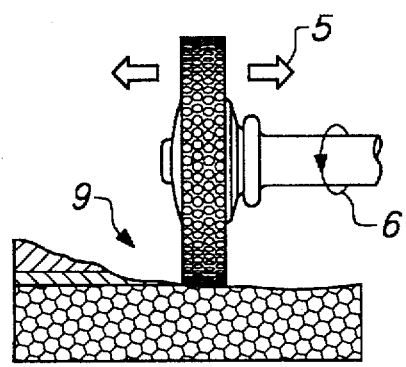
FIG. 7 is a schematic of the application method of the invention presenting the means to contour bone surface(9).

Referring now to FIG. 7, a schematic view of the preferred method the current invention is applied to contour bone(3) where the bone brush, after being attached to a surgical rotary hand piece, is rotated in a circular manner(6) and applied to soft tissue covering of bone in a back and forth manner(5) thereby removing the soft tissue(1) and cortical bone(2) from cancellous bone(3) in a manner that provides various shapes(9) of bone.

To those skilled in the art to which the present invention pertains, many widely varying embodiments and implementations of the principals of the present invention will be suggested from the foregoing. For instance, the bone brush head may be changed in diameter and shape. Accordingly, the materials used to manufacture the bone brush may be changed or coated with another material. Additionally, the size and number of brush fibers may be changed as desired. The description of the disclosures present herein are by way of illustration only and should not be considered to limit the present invention, the scope of which is more particular set forth in the following claims.

What is claimed is:

1. A method of preparing host and graft bone surfaces during a surgical bone graft procedure, the method comprising the steps of:

providing a rotary bone brush device comprised of materials suitable for use within human body during surgical procedures, the bone brush device comprising a shaft, a brush head including a plurality of fibers arranged for rotary engagement with a bone, and a brush cap assembly mounted on the shaft, the brush cap assembly including a locking ring that secures the plurality of fibers around the shaft, the rush cap assembly also including a top locking cap and a bottom locking cap which are attached to the shaft and secure the locking ring and the plurality of fibers;

causing the device to rotate;

applying the device to a surface of a bone;

moving the device along the bone during rotation of the device to remove soft tissue from the bone;

moving the device along the bone during the rotation of the device to decorticate cancellous bone; and moving the device along the bone during the rotation of the device to contour the bone.

2. The method of claim 1 wherein the fibers, shaft, top and bottom caps and locking ring of the bone brush device are made of surgical grade stainless steel.

3. The method of claim 1 wherein the causing the device to rotate step comprises the use of a surgical rotary hand piece attached to the shaft of the bone brush device.

4. The method of claim 3 wherein the speed of rotation of the shaft and brush head is controlled by the rotary hand piece.

* * * * *